US008205808B2

(12) United States Patent
Leer et al.

(10) Patent No.: US 8,205,808 B2
(45) Date of Patent: Jun. 26, 2012

(54) PRESSURIZED TANK SPRAYER HAVING LID SEAL

(75) Inventors: Rick L. Leer, Somerset, PA (US); Timothy S. DeVore, Rockwood, PA (US); Thomas C. Oyler, Louisville, KY (US)

(73) Assignee: Robert Bosch GmbH, Stuttgart, DE (US)

( * ) Notice: Subject to any disclaimer, the term of this patent is extended or adjusted under 35 U.S.C. 154(b) by 311 days.

(21) Appl. No.: 12/217,929

(22) Filed: Jul. 9, 2008

(65) Prior Publication Data

US 2008/0272210 A1 Nov. 6, 2008

Related U.S. Application Data

(63) Continuation of application No. 10/933,973, filed on Sep. 3, 2004, now abandoned.

(51) Int. Cl.
*A61M 11/02* (2006.01)
*A01G 25/14* (2006.01)
*B65D 83/00* (2006.01)

(52) U.S. Cl. ......... 239/333; 239/373; 239/375; 222/401

(58) Field of Classification Search .................. 239/373, 239/375, 337, 333; 222/258, 395, 401; 277/647, 277/549, 491, 436, 395
See application file for complete search history.

(56) References Cited

U.S. PATENT DOCUMENTS

| | | | | |
|---|---|---|---|---|
| 1,557,650 A | | 10/1925 | Brandt | |
| 2,180,664 A | * | 11/1939 | Brandt | 222/384 |
| 2,529,645 A | | 11/1950 | Winks et al. | |
| 2,544,854 A | | 3/1951 | Oys et al. | |
| 2,608,318 A | | 8/1952 | Keller | |
| 2,660,330 A | | 11/1953 | Keller | |
| 2,794,452 A | | 6/1957 | Quam | |
| 3,127,049 A | * | 3/1964 | Welty et al. | 220/301 |
| 3,135,431 A | | 6/1964 | Matthewson et al. | |
| 3,584,769 A | * | 6/1971 | Pinke | 222/340 |
| 3,709,409 A | * | 1/1973 | Collins | 222/402 |
| 3,941,268 A | | 3/1976 | Owens et al. | |
| 4,154,401 A | | 5/1979 | Thompson | |
| 4,192,464 A | | 3/1980 | Chow | |
| 4,400,020 A | | 8/1983 | Keller | |
| 4,537,334 A | | 8/1985 | Spengler et al. | |

(Continued)

OTHER PUBLICATIONS

Gardena instruction manual; published at least as early as Sep. 2, 2004; six pages.

*Primary Examiner* — Jason J Boeckmann
*Assistant Examiner* — Justin Jonaitis
(74) *Attorney, Agent, or Firm* — Maginot, Moore & Beck

(57) ABSTRACT

A pressurized tank sprayer includes a base tank including a neck and a mouth. A lid having a top portion and a depending skirt is positioned upon the tank. Threads are provided on the neck of the tank and engage threads on the depending skirt of the lid in order to secure the lid to the tank. The threads include locking features that prevent the lid from becoming forcibly detached from the tank during removal of the lid if excess pressure remains in the tank. An annular seal is seated in the lid and provides a seal between the tank and the lid. The annular seal includes an annular sealing surface and a concave interior surface. The annular sealing surface contacts the interior surface of the tank while the concave interior surface is exposed to the interior of the tank.

16 Claims, 12 Drawing Sheets

U.S. PATENT DOCUMENTS

| | | | |
|---|---|---|---|
| 4,770,308 A | 9/1988 | Lynn | |
| D312,297 S | 11/1990 | Ballu | |
| 4,984,742 A | 1/1991 | Ellison | |
| 5,072,884 A | 12/1991 | Ellison et al. | |
| 5,169,033 A | 12/1992 | Shay | |
| 5,186,391 A | 2/1993 | Roueche et al. | |
| 5,307,995 A | 5/1994 | Jackson et al. | |
| 5,462,186 A | 10/1995 | Ladina et al. | |
| 5,676,270 A | 10/1997 | Roberts | |
| 5,676,314 A | 10/1997 | Brass et al. | |
| 5,755,361 A * | 5/1998 | Restive et al. | 222/209 |
| 5,845,798 A | 12/1998 | Carrier | |
| 5,868,273 A | 2/1999 | Daenen et al. | |
| 5,924,633 A | 7/1999 | Brass et al. | |
| 6,113,003 A | 9/2000 | Condon | |
| 6,155,497 A | 12/2000 | Hudson, Jr. et al. | |
| 6,354,601 B1 | 3/2002 | Krampotich et al. | |
| 2003/0019954 A1 | 1/2003 | Clarke | |
| 2003/0102335 A1 | 6/2003 | Barnett | |

* cited by examiner

PRESSURIZED TANK SPRAYER HAVING LID SEAL

BACKGROUND

This invention relates to the field of pressurized tank sprayers used for dispensing a fluid from a tank.

Pressurized tank sprayers are common tools in households throughout the world. These tank sprayers are typically used by individuals to disperse chemicals for lawn care, pest control, or other residential concerns.

Pressurized tank sprayers typically include a tank for holding chemicals and a lid that seals the tank air-tight. A hand pump is generally incorporated on the apparatus for introducing air into the sealed tank. Also, a hose is provided for channeling chemicals within the tank to a nozzle attached to the end of the hose. The user operates the hand pump to force air into the sealed tank, thereby increasing the pressure in the tank. The increased pressure in the tank forces the chemicals or other liquid in the tank through the hose and out the nozzle when the nozzle is operated.

A number of potential problems exist with the design of typical tank sprayers. First, if the tank is not adequately sealed, it will not retain pressure and will not be able to force liquid through the hose and out the nozzle. Therefore, a good seal between the lid and tank is required. O-ring seals are often used to provide the seal between the lid and the tank in pressurized tank sprayers. A significant amount of force is typically required to adequately compress the O-ring and establish a seal in these sprayers. Unfortunately, many individuals are not strong enough to compress the lid to the tank in a manner that provides a good O-ring seal. Accordingly, it would be desirable to provide a pressurized tank sprayer requiring less force to properly seal the lid to the tank.

Another problem with previous pressurized tank sprayers is that a user of the sprayer may fail to open the pressure relief valve and relieve the pressure from the tank before attempting to remove the lid from the tank. When the user forgets to properly relieve the increased pressure in the tank before attempting to remove the lid, the pressure within the tank may cause the lid to become forcibly detached from the tank during such removal attempt. Therefore, it would be desirable to provide a pressurized tank sprayer having a safety feature that automatically relieves excess pressure within a tank when a user is attempting to remove the lid from the pressurized tank.

SUMMARY

A pressurized tank sprayer with annular seal comprises a tank, a removable lid and an annular seal. The tank includes an interior surface and an exterior surface. A mouth is formed in the tank and provides communication between the interior and the exterior of the tank. The tank further includes a neck portion that leads to and defines the mouth. The removable lid is secured to the tank and covers the mouth. The removable lid includes a top with a depending skirt. The removable lid also includes an annular groove designed to receive the annular seal.

The annular seal is disposed between the tank and the lid when the lid is positioned upon the tank. The annular seal includes a collar that is retained by the annular groove on the lid. The annular seal also includes an annular sealing surface and an interior concave surface. The annular sealing surface and the interior surface of the lid skirt define an annular channel that receives the neck portion of the tank when the removable lid is secured upon the tank. In particular, when the neck portion of the tank is positioned in the annular channel, an exterior surface of the neck portion contacts the interior surface of the skirt and an interior surface of the neck portion contacts the annular sealing surface of the annular seal. The interior concave surface of the annular seal is exposed to the interior of the tank when the lid is secured to the tank.

In one embodiment, the exterior surface of the neck portion of the tank includes a first plurality of threads, and the interior surface of the lid skirt includes a second plurality of threads. The first plurality of threads is operable to move in rotatable engagement relative to the second plurality of threads. Also, the first plurality of threads is operable to move in rotatable disengagement relative to the second plurality of threads. The first plurality of threads and the second plurality of threads include means for permitting an axial shift of the first plurality of threads relative to the second plurality of threads in response to an increased pressure within the tank during rotatable disengagement of the first plurality of threads relative to the second plurality of threads. This axial shift permits the increased pressure to be released from the tank without disengagement of the first plurality of threads from the second plurality of threads.

DESCRIPTION

Figure 1:
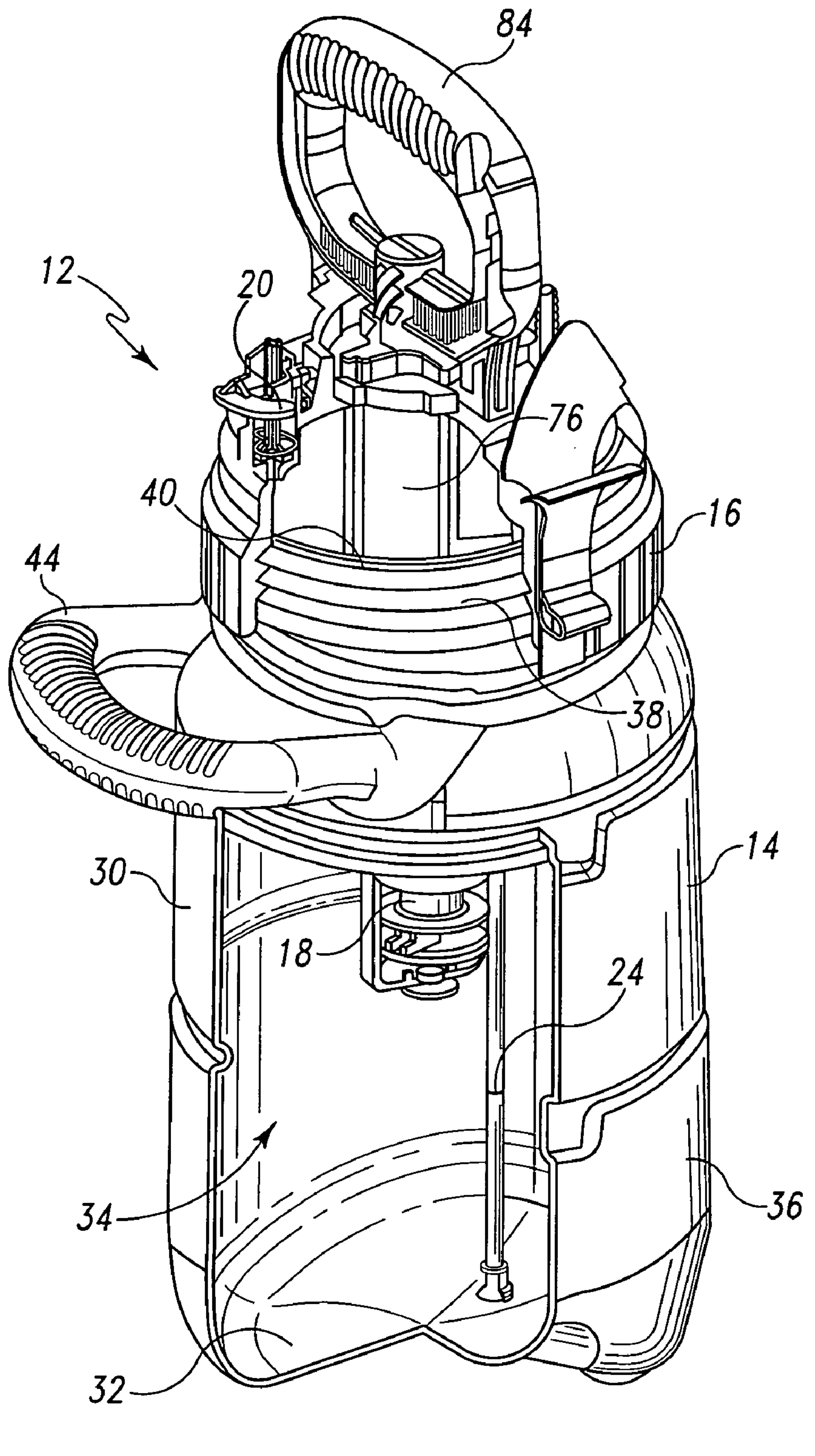
FIG. 1 is a top perspective view of a pressurized tank sprayer with an annular seal that incorporates the features of the present invention therein, and showing a tank and lid together, with a cutaway view of a tank interior and a cutaway view of the lid.
Figure 2:
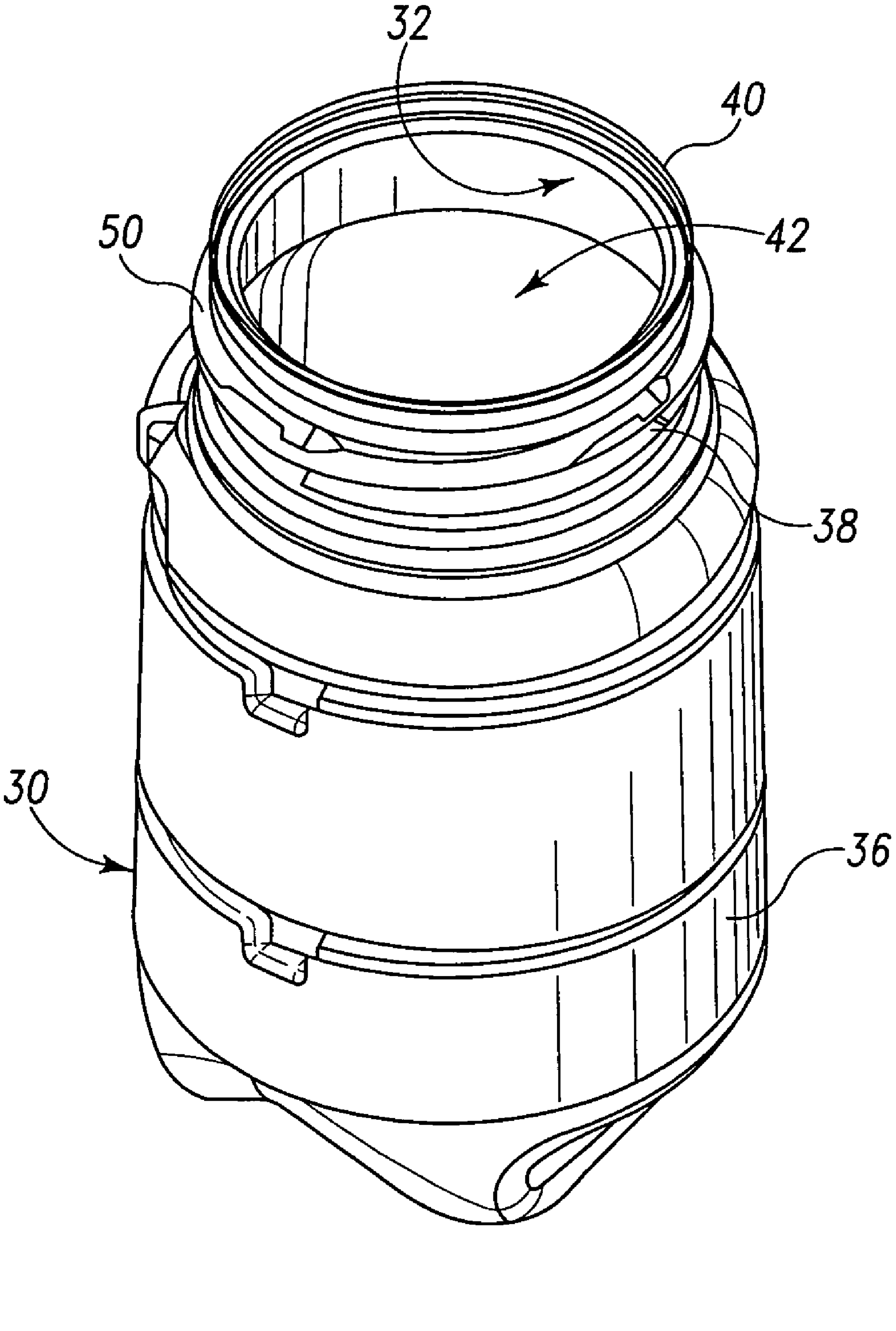
FIG. 2 is a top perspective view of the tank of the pressurized tank sprayer of FIG. 1.

With reference to FIGS. 1 and 2, a pressurized tank sprayer 12 is shown. The pressurized tank sprayer includes a base tank 14 and a lid 16 positioned upon the tank. A pump 18 is formed in the lid 16 along with a pressure release valve 20. An outlet port 22 is also positioned on the lid 16. A tube 24 extends between the outlet port and the bottom of the tank 14.

A hose 26 and nozzle 28 (see FIG. 3) are attached to the exterior of the outlet port 22. The pump 18 is used to pump air into the tank 14, thereby increasing the pressure in the tank. When the nozzle is actuated, the pressure in the tank 14 forces liquid contents of the tank through the tube 24, past the outlet port 22, and through the hose 26 and nozzle 28.

The tank 14 includes an exterior surface 30 and an interior surface 32. The tank is designed to hold liquid to be sprayed from the tank. The tank interior surface 32 defines a chamber 34 having a volume for holding liquid. The tank includes a lower body portion 36 and a neck 38. The neck 38 is generally tapered or otherwise smaller in diameter than the lower body portion 36 of the tank. However, one of ordinary skill in the art will recognize that the neck 38 may have a diameter equal to the lower body portion 36, or may be flared with a diameter greater than the lower body portion. A plurality of threads 50 are disposed upon and spiral around the neck 38. The top of the neck 38 leads to a top rim 40. The top rim 40 defines a mouth 42. The mouth 42 provides an opening between the interior of the tank and the exterior of the tank. This opening is used for communication of liquids into or out of the tank chamber 34. The tank is generally comprised of a lightweight material such as plastic. However, the tank may also be comprised of any number of other materials suitable for holding liquid, such as glass or metal.

A side carry handle 44 may be included on the tank, as is shown in FIG. 1. The side carry handle 44 may be used to stabilize the tank when the lid is being attached to or removed from the tank. In addition, the side carry handle provides a convenient location from which the user may carry the tank and/or manipulate the tank during cleaning.

Figure 3:
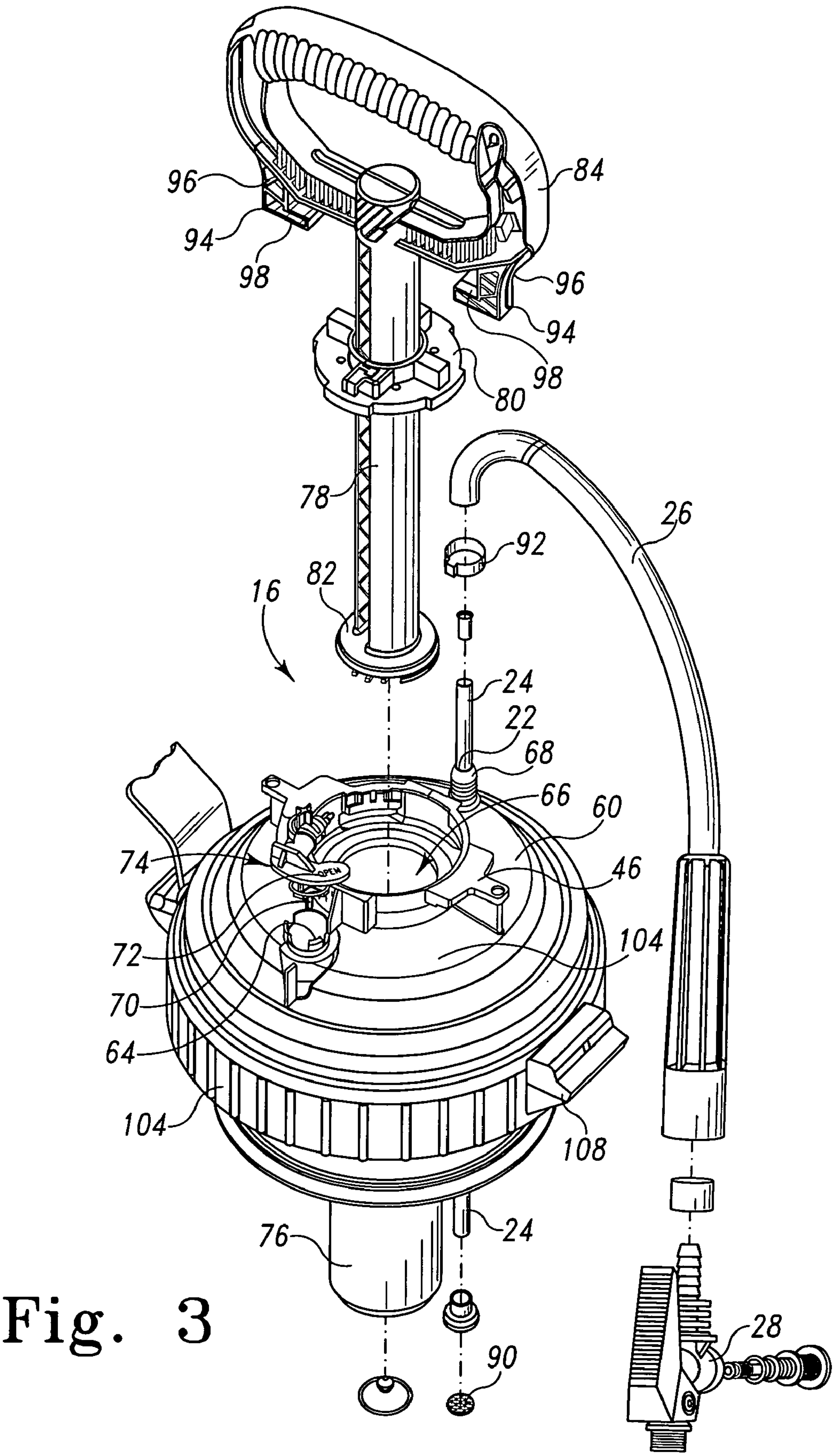
FIG. 3 is a perspective exploded assembly view of the lid of the pressurized tank sprayer of FIG. 1.
Figure 4:
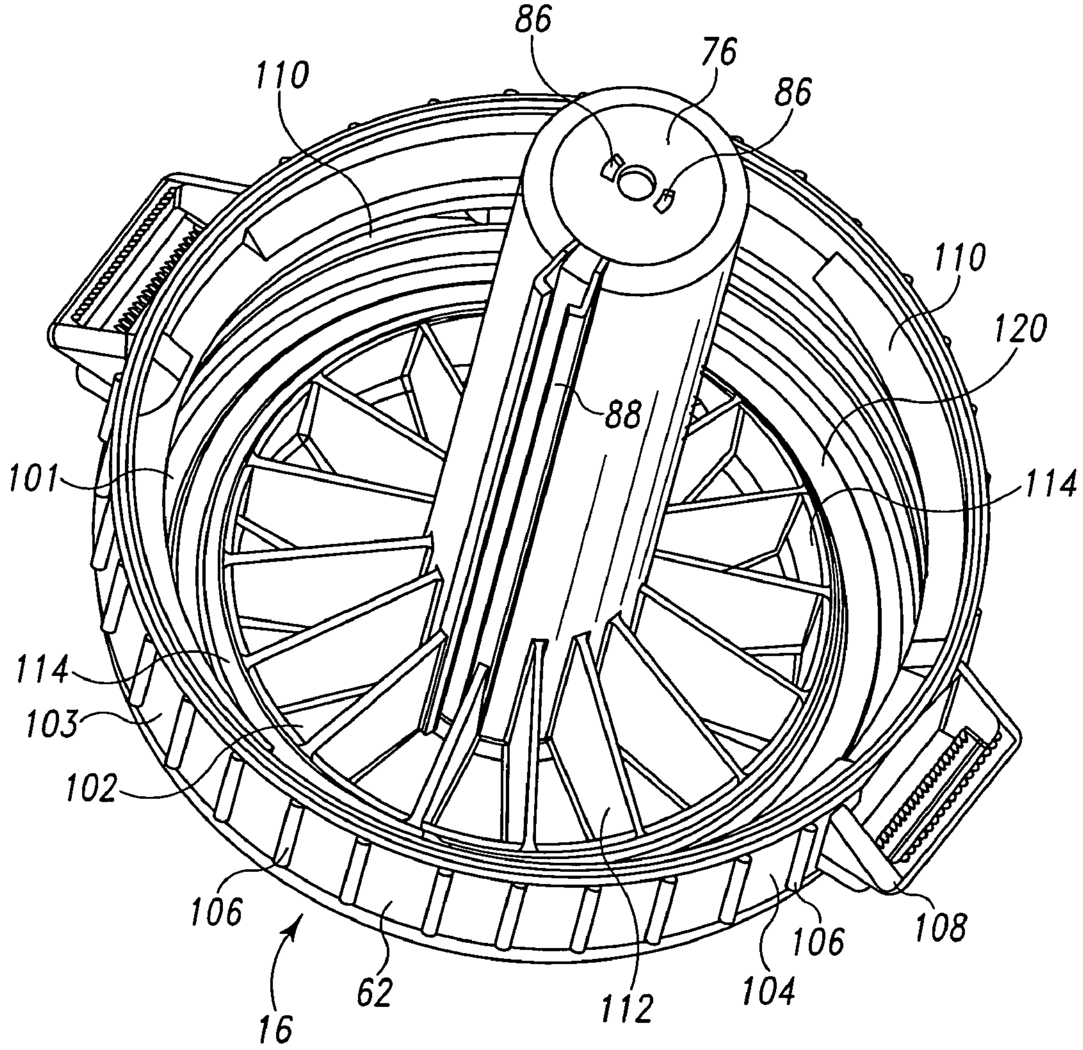
FIG. 4 is a perspective view of the lid of the pressurized tank sprayer of FIG. 1.
Figure 5:
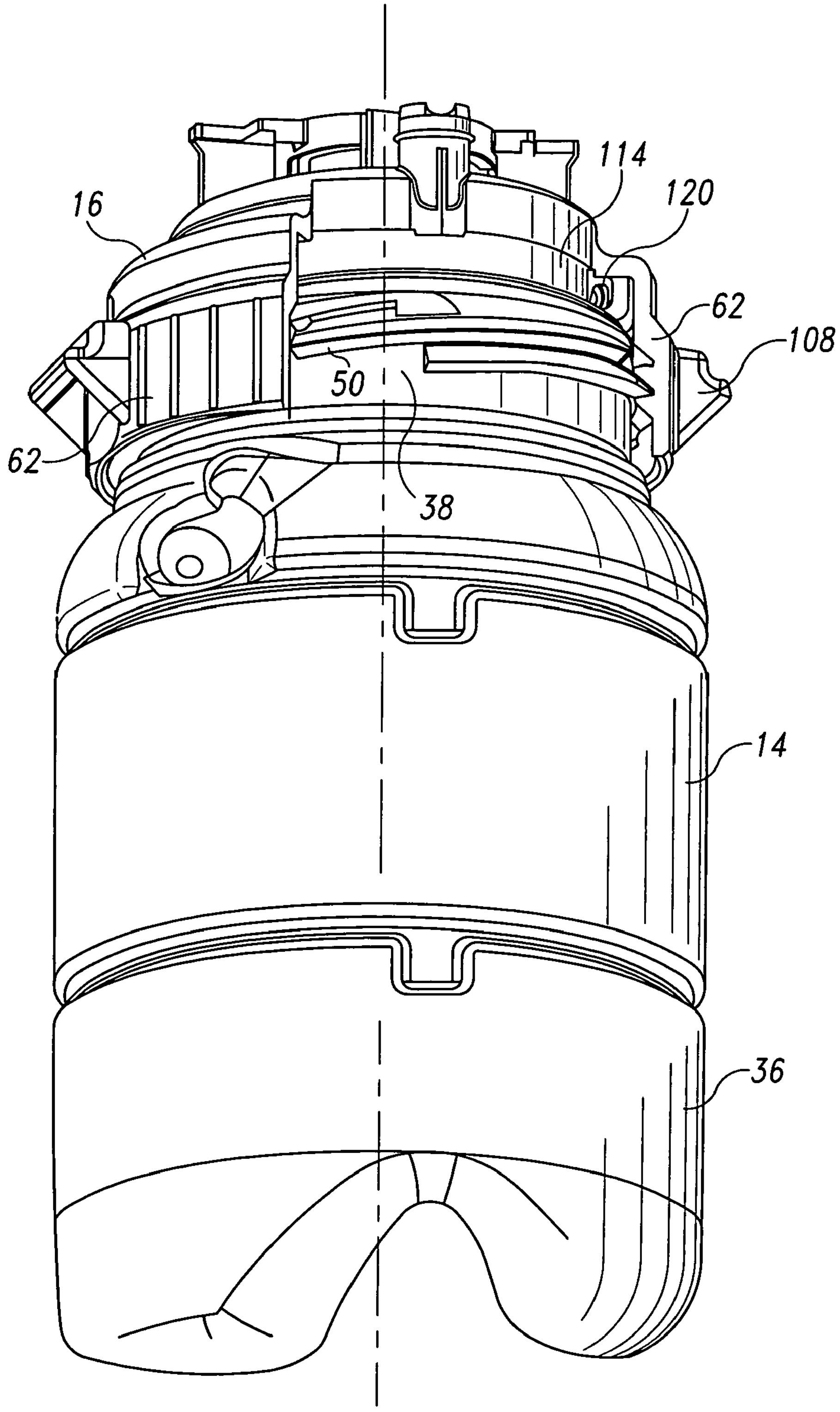
FIG. 5 is a side perspective view of the tank of the pressurized tank sprayer of FIG. 1 showing a cutaway view of the threads on the tank and the lid.
Figure 6:
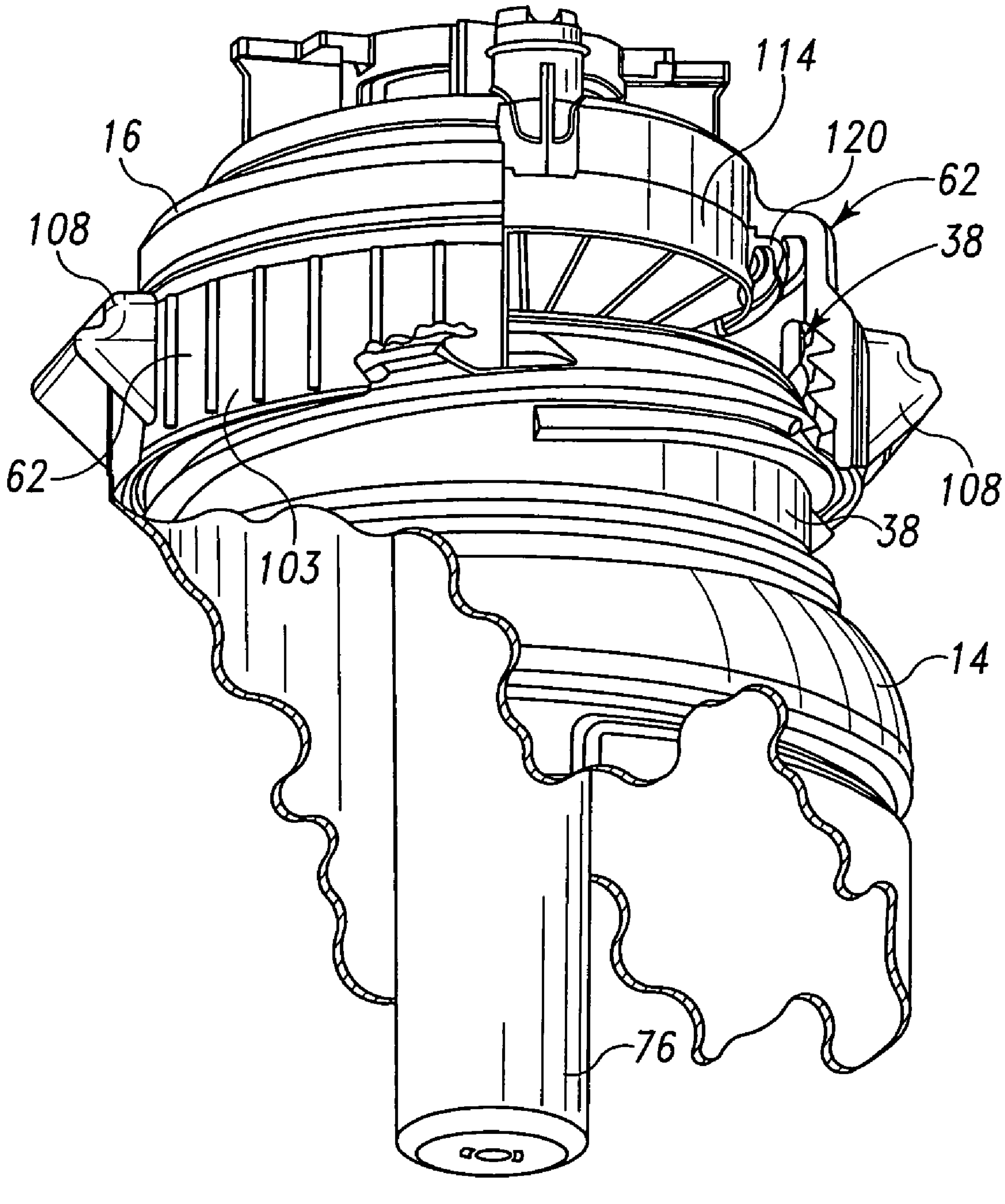
FIG. 6 is another side perspective view of the pressurized tank sprayer of FIG. 1 showing a cutaway of the lid as it is removed from the tank and showing an annular sealing ring seated in the lid.

With reference to FIGS. 3 and 4, the lid 16 is generally formed of a plastic material and includes a top 60 with a depending annular skirt 62. The top 60 of the lid includes a pressure relief port 64, a pump opening 66 and a fluid outlet port 68. The top of the lid 60, skirt 62, pressure relief port 64, pump opening 66 and fluid outlet port 68 are all molded as a single integral unit.

The pressure relief port 64 is designed and dimensioned to receive a pressure relief valve 70. The pressure relief valve includes a lever 72 operable to open and close the pressure relief valve 70. The lever pivots 180° about a pivot point 74 between an open position and a closed position. When the lid 16 is secured to the tank 14 and the lever is in the open position, the pressure relief valve 70 is open. With the pressure relief valve open, a passage is provided allowing pressurized air/gas within the tank to escape the tank through the pressure relief valve 70. On the other hand, when the lever 72 is in the closed position, the pressure relief valve 70 is closed. With the pressure relief valve 70 closed, the passage through the pressure relief valve 70 is blocked, thereby preventing pressurized air/gas within the tank from escaping the tank though the pressure relief valve.

The pump opening 66 in the lid 16 is designed and dimensioned to receive a pump plunger 78 and pump cap 80. The pump opening 66 feeds into an elongated pump cylinder 76 integrally formed with the lid 16. The pump cylinder 76 extends downward into the interior of the tank 14 when the lid 16 is placed on the tank. A plurality of holes 86 are formed at the bottom of the pump cylinder 76. The cap 80 fits over the pump opening 66 in the lid and is fixed to the lid to secure the pump plunger 78 on the lid. The pump plunger 78 slideably engages the cap 80, allowing the plunger 78 to move up and down with respect to the lid 16 and the cap 80. A piston 82 is attached to the bottom end of the plunger 78 and is retained within the cylinder 76. A handle 84 is attached to the top end of the plunger. The handle allows manual operation of the pump. In particular, upward movement of the handle 84 moves the plunger 78 and attached piston 82 upward within the cylinder 76. As the piston 82 is moved upward, a valve (not shown) positioned upon the piston allows air to rush into the cylinder on the bottom side of the piston. Thereafter, downward movement of the handle forces the plunger and attached piston downward in the cylinder. When the piston moves downward, the valve is closed, forcing air out of the holes 86 in the bottom of the cylinder. In this manner, air may be forced into the tank 14 in order to pressurize the tank.

With continued reference to FIG. 3, the pump handle 84 includes two hooks 94 that depend from the bottom of the handle. Each hook 94 includes a downward extending portion 96 and a cross member 98. Two shelves 46 are formed on the top 60 exterior surface of the lid 16. Each shelf 46 provides a contact surface designed and dimensioned to receive the hooks 94 on the pump handle 84 such that the cross member 98 of each hook can be positioned under the shelf. Also, each shelf 46 includes a side flange 48 that depends downward from the shelf 46. A spring (not shown) is provided in bottom of the pump cylinder 76. The spring is designed to contact the piston 82 when it reaches the bottom portion of the cylinder 76, thereby preventing the piston from resting on the bottom of the cylinder when the piston is fully depressed in the cylinder. This spring also biases the piston and pump plunger 78 slightly upward when the piston is near the bottom of the cylinder. In particular, if the handle 84 is used to push the piston 82 to the bottom of the cylinder 76, and the handle is then released, the spring will press against the piston and bias the piston and plunger slightly upward. Together, the spring, hooks and shelf provide a stationary rest for the handle. In order to place the handle in the stationary rest, the user first moves the handle 84 downward such that the piston 82 compresses the spring in the cylinder 76. Next, the handle 84 is rotated so the cross members 98 of the hooks 94 are positioned under the shelves 46. Finally, the user releases the handle 84, allowing the spring to move the piston 82, plunger 78 and connected handle 84 slightly upward so the cross members 98 on the hooks 94 contact the lower surface of the shelf 46. The flanges 48 retain the hooks 94 and connected handle 84 in place under the shelf 46 until the user forces the handle downward again and rotates the cross members 98 of the hooks under the shelf and depending flanges, thereby freeing the handle for pumping action.

The fluid outlet port 68 is also positioned on the top of the lid 16 and provides an opening in the lid. The tube 24 extends through the bottom side of the fluid outlet port 68. The cylinder 76 includes an exterior track 88 for receiving the tube and holding it in place within the tank. A screen filter 90 is positioned at the bottom of the tube 24 for blocking solid particles from passing into the tube that may be large enough to clog or otherwise damage the nozzle 28. One end of the hose 26 is attached to the nozzle 28. The opposite end of the hose is attached to the top of the exterior surface of the fluid outlet port 68. A clamp 92 is used to secure the hose 26 to the fluid outlet port 68.

The skirt 62 of the lid 16 depends from the top 60 of the lid in an annular fashion. The skirt includes an interior surface 101 and an exterior surface 103. The interior surface 101 of the skirt defines a portion of an interior lid surface 102, and the exterior surface 103 of the skirt defines a portion of an exterior lid surface 104. The exterior lid surface 104 includes handles 108 as well as a plurality of gripping bars 106. The handles 108 may be used to carry the pressurized tank sprayer 12, and may also be used along with the gripping bars 106 when twisting the lid 16 on or off of the tank 14.

The interior lid surface 102 is best viewed with respect to FIG. 4. As mentioned previously, the cylinder 76 extends from the center of the lid interior. A plurality of ribs 112 extend from the cylinder 76 toward the skirt 62, but do not extend to the skirt. Instead, the ribs 112 extend to an annular wall 114 which is concentric with the cylinder. The annular wall 114 is also concentric with the skirt 62. The annular wall depends from the top 60 of the lid, but does not extend downward as far as the skirt 62. A plurality of skirt threads 110 spiral around the interior surface of the skirt. The plurality of skirt threads are designed to engage the plurality of neck threads on the tank, thereby securing the lid to the tank.

Figure 7:
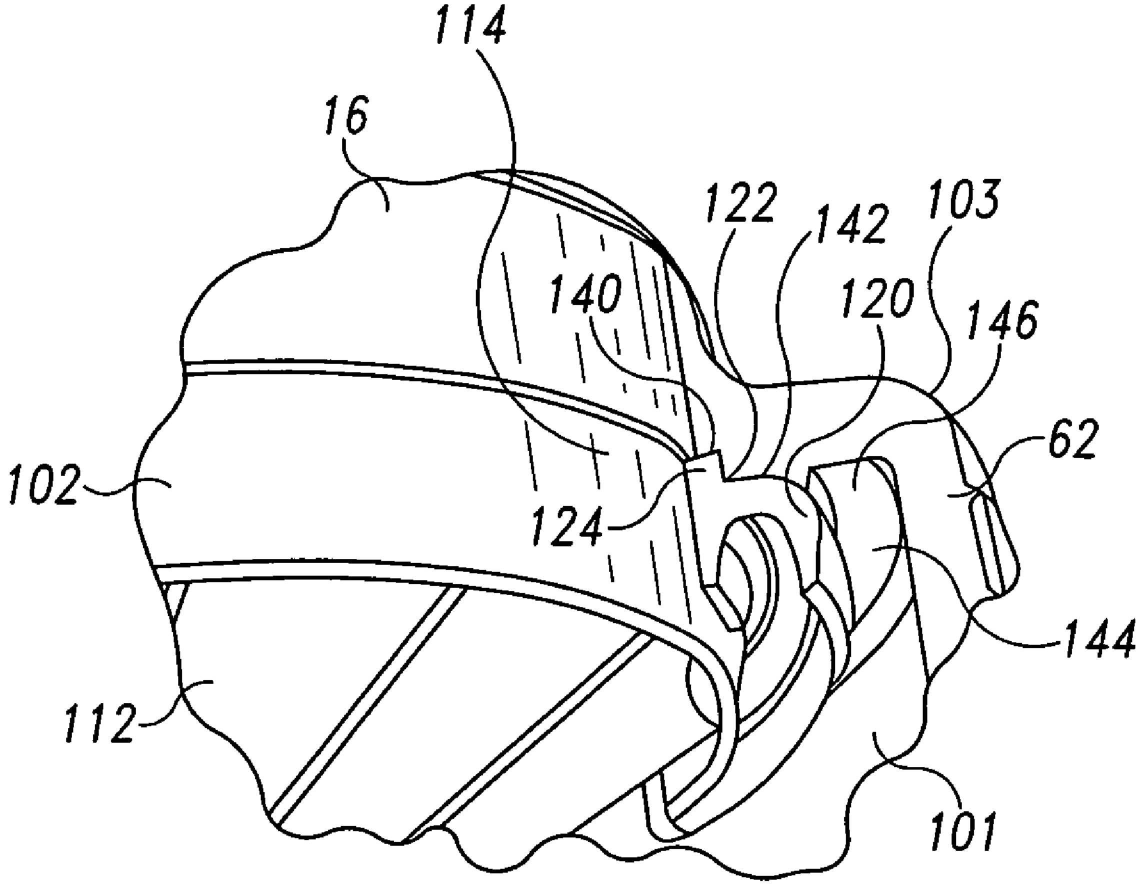
FIG. 7 shows an enlarged perspective view of the annular sealing ring of FIG. 6.
Figure 8:
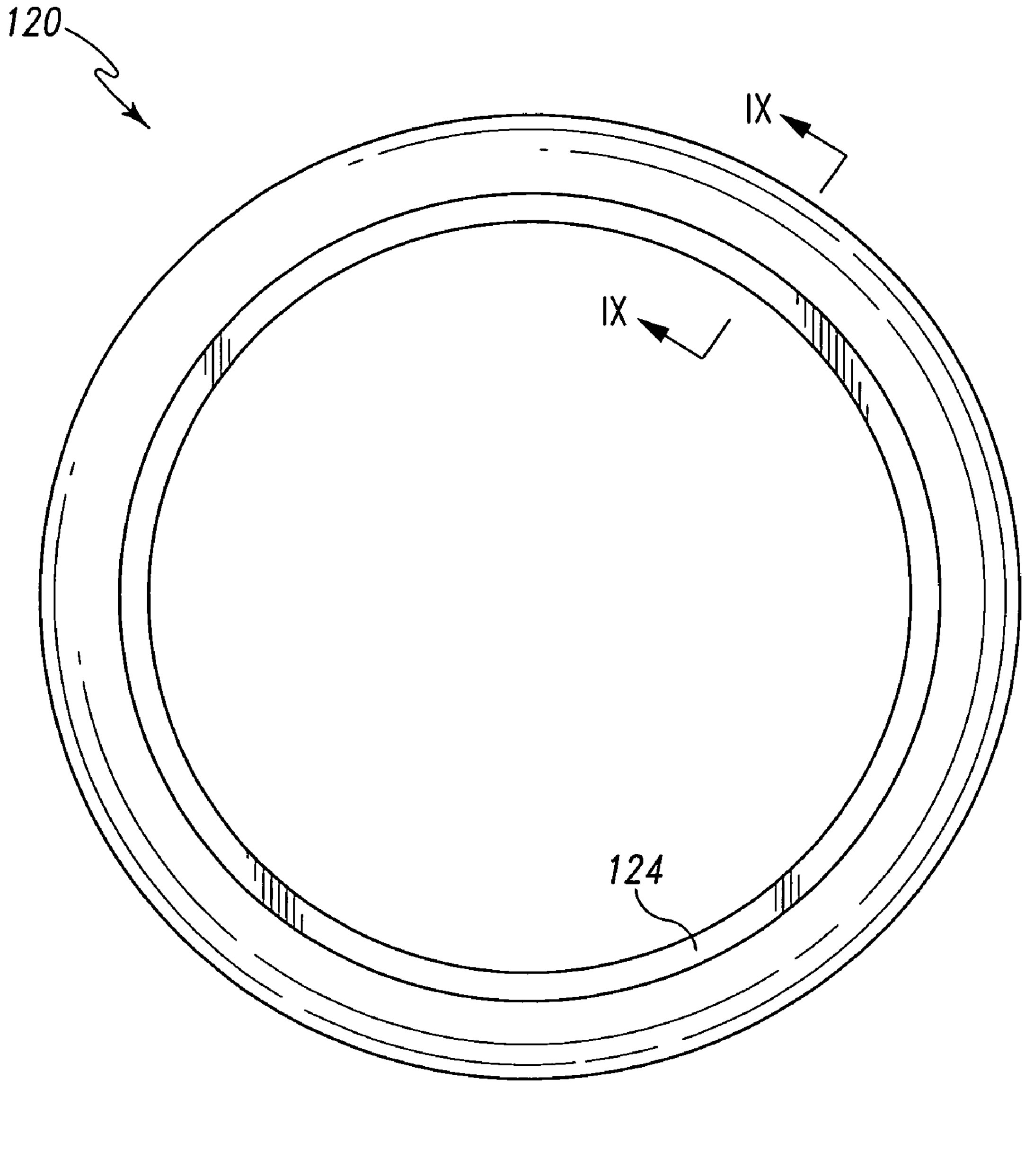
FIG. 8 shows a top plan view of the annular sealing ring of FIG. 7.
Figure 9:
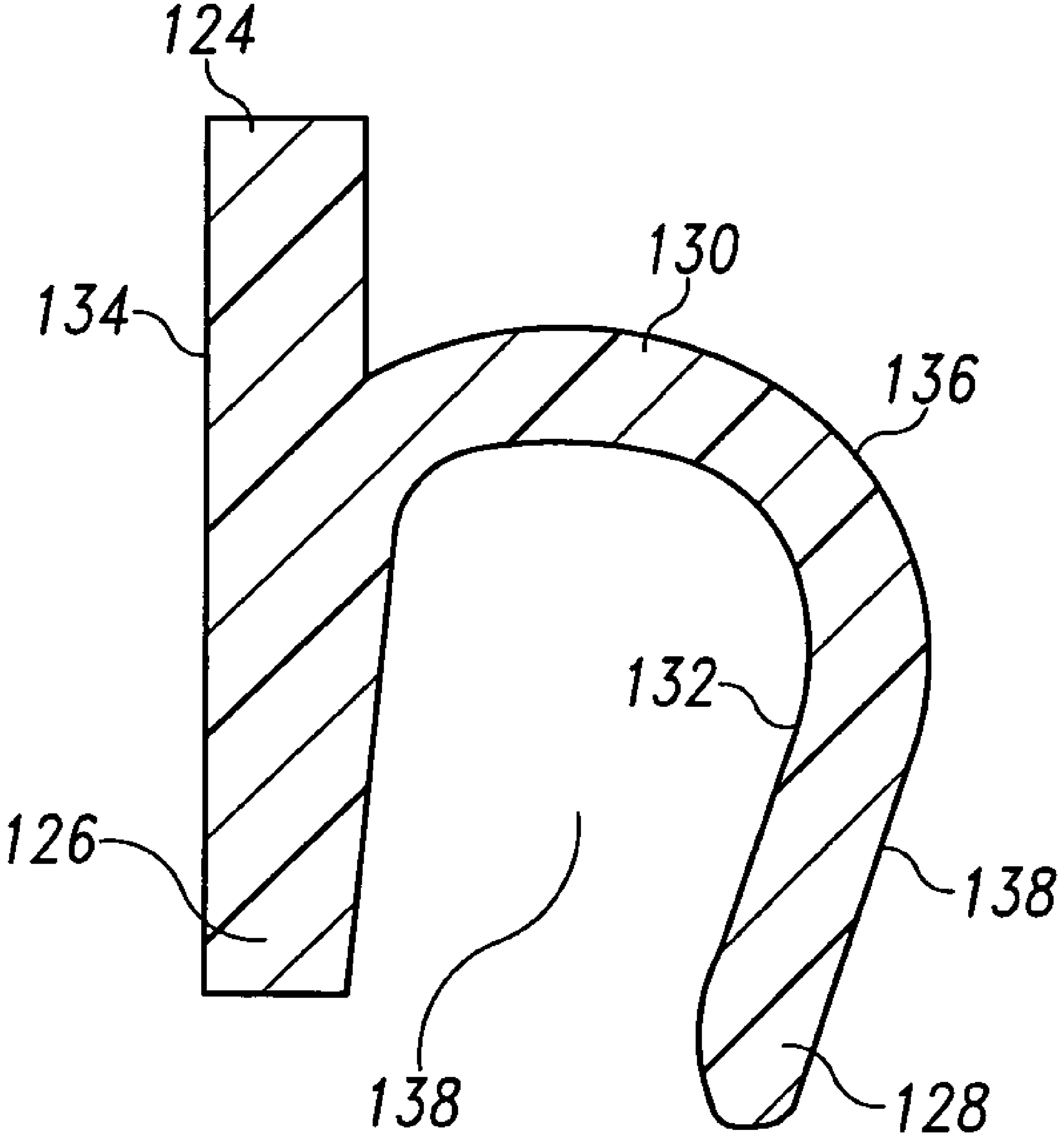
FIG. 9 shows a cross-sectional view of the annular sealing ring along line IX-IX of FIG. 8.

With reference to FIGS. 6-9, an annular seal 120 is retained upon the lid 16. The seal 120 is retained upon the lid 16 in a seal seat 122 which is formed on the interior surface 102 of the lid. The annular seal 120 is generally ring-shaped, as shown in FIG. 8. The annular seal is made of a resilient material, such as a soft rubber material, and is formed as a single integral piece. As shown in FIGS. 6, 7, 9, and 10, the seal 120 has a generally "h" shaped cross section. The seal 120 includes an interior lip 126 and an exterior lip 128 joined by a curved upper body portion 130. An annular collar 124 is formed adjacent to the interior lip 126 and the upper body portion 130. The annular collar extends upward above the interior lip 126 and the upper body portion 130. The top of the annular collar has a generally rectangular cross-section. A concave interior surface 132 is defined by the interior lip 126, exterior lip 128 and upper body portion 130. The concave interior surface is U-shaped, and forms an annular trench 138 within the seal 120. A flat seating surface 134 is defined by the interior lip 126 and the top collar 124. A convex exterior surface 136 is defined by the exterior lip 128 and the upper body portion 130. As explained in further detail below, the convex exterior surface 136 provides an annular sealing surface 136 that contacts the tank 14. As shown in FIG. 9, the lower portion of the annular sealing surface 136 that forms the exterior lip 128 includes a flat portion 138.

Figure 10:
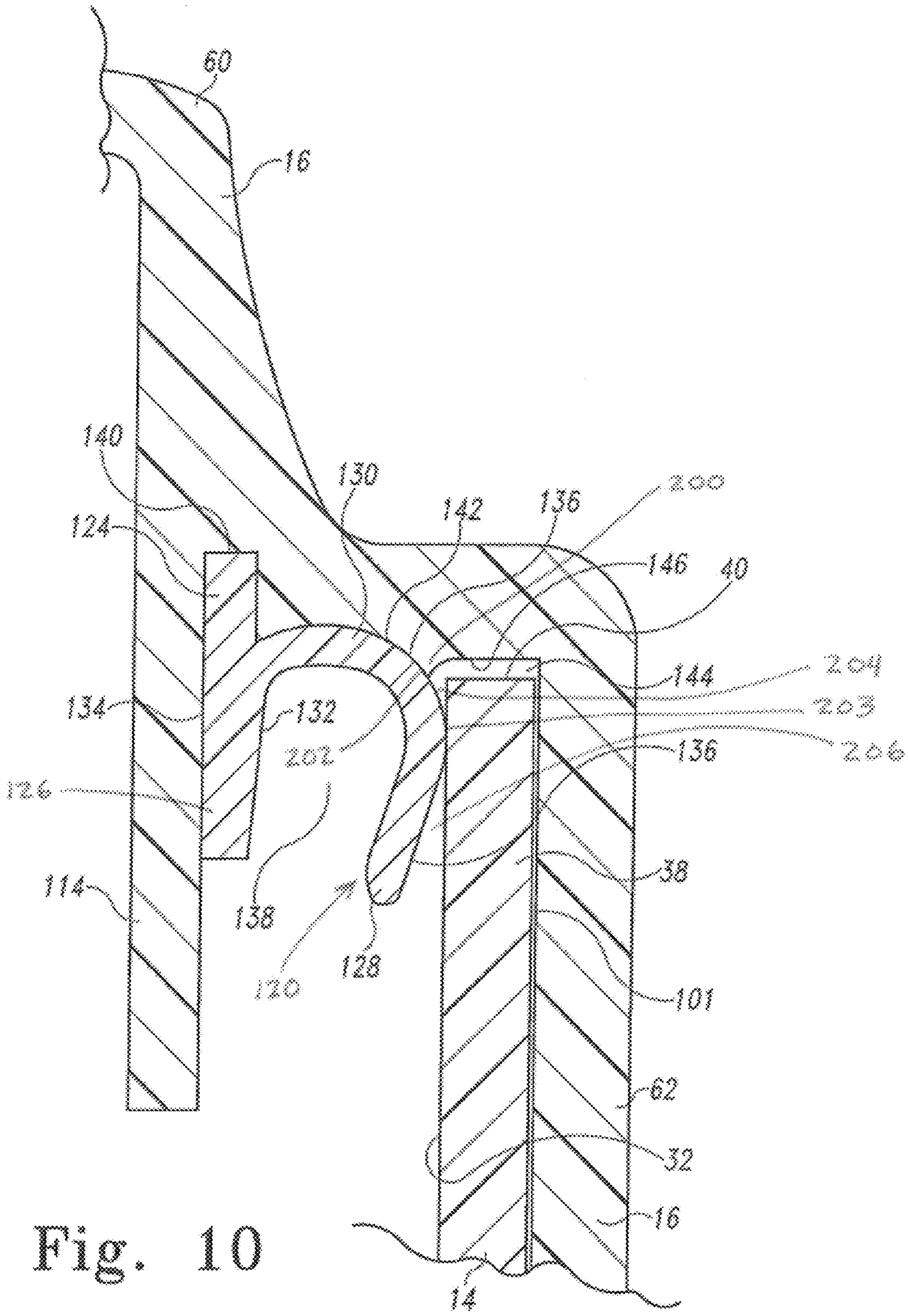
FIG. 10 shows a cross-sectional view of the annular sealing ring of FIG. 7 seated within the lid and in contact with the tank.

As shown in FIG. 10, it can be seen that the top portion of the lid 16 includes a ramp structure 200 that projects into the space defined between the annular wall 114 and the skirt 62 so as to define a ramped seal seat surface 202. When (i) the curved upper body portion 130 is positioned in contact with the ramped seal seat surface 202, and (ii) the interior lip 126 is positioned in contact with the annular wall 114, it can be seen that the seal 120 extends beyond the ramped seal seat surface 202 so as to position the exterior lip 128 in contact with the neck portion of the tank 14 at a seal location 203. As also can be seen in FIG. 10, a first gap 204 is defined between the exterior lip 128 and the neck portion of the tank 14 on a first side of the seal location 203, while a second gap 206 is defined between the exterior lip 128 and the neck portion on a second opposite side of the seal location 203.

With reference to FIGS. 7 and 10, the seal seat 122 provided by the lid 16 includes an annular groove 140 formed in the lid around the annular wall 114. The annular groove 140 is designed and dimensioned to snugly receive the annular collar 124 of the seal 120. The seal seat 122 also includes a transverse support surface 142. The transverse support surface 142 is concave and extends laterally away from the annular groove 140. When the seal 120 is positioned in the seal seat, the seal collar 124 is snugly held within the annular groove 140 in the lid. At the same time, the flat seating surface 134 of the seal 120 is flush against the annular wall 114 in the lid. Furthermore, the curved upper portion 130 of the concave exterior surface 136 of the seal 120 is in contact with the concave transverse support surface 142. The lower portion of the concave exterior surface 136 of the seal extends downward from the transverse support surface 142, such that the exterior lip 128 of the seal is free to move back and forth in the radial direction. An annular channel 144 is formed between the exterior surface 136 of the seal 120 and the interior surface 101 of the skirt 62 which depends from the top 60 of the lid 16. A channel ceiling 146 is provided by the top interior surface 102 of the lid.

As shown in FIG. 10, the annular seal 120 serves to provide a seal between the lid 16 and the tank 14. In particular, as the lid 16 is positioned on the tank 14, the threads on the neck of the tank rotatably engage the threads on the skirt of the lid and draw the lid downward upon the neck 38 and top rim 40 of the tank. As the threads near full engagement, the neck 38 of the tank enters the annular channel 144 formed between the seal 120 and the interior surface of the skirt 62. When the neck 38 of the tank enters the annular channel 144, the interior surface 32 of the neck contacts the annular sealing surface 136 of the seal 120. As the neck 38 passes further into the annular channel 144, the force of the neck against the annular sealing surface 136 causes the seal to slightly deform. However, relatively little force in addition to the rotational force required for thread engagement is required from the user to force the neck 38 of the tank into the annular channel 144 formed in the lid and against the annular sealing surface 136. Because the seal 120 is resilient, the deformed annular sealing surface 136 presses against the tank and forms a seal with the tank. While the exterior lip of the seal 120 is allowed to deform and shift to form the seal, the other portions of the seal 120 remain substantially stationary in the seal seat, pressed against the annular wall 114, annular groove 140 and transverse support surface 142. Once the top rim 40 of the tank contacts the channel ceiling 146, the further engagement of the neck 38 of the tank into the annular channel 144 in the lid is prohibited. However, the top rim 40 of the tank need not contact the channel ceiling 146 for proper sealing between the tank and lid to occur. For example, further engagement of the neck into the annular channel 144 may be prohibited upon full and complete engagement of the neck threads with the skirt threads.

With the lid 16 secured on the tank 14, the annular seal 120 is in contact with and sealed against the tank interior surface 32, as discussed above. Accordingly, the U-shaped interior surface 132 of the annular seal 120 is exposed to the interior of the tank along with the associated annular trench 138. When pressure is introduced into the tank interior that is greater than the atmospheric pressure experienced on the outside of the tank, the pressure provides an outward force on the interior surface of the tank. This pressure also provides an outward force on the U-shaped interior surface 132 of the annular seal, since it is exposed to the tank interior. The outward force on the interior surface 132 of the annular presses the annular sealing surface 136 against the interior surface of the tank 32 and helps maintain the seal between the lid 16 and the tank 14 when the tank is pressurized.

In order to remove the lid 16 from the tank 12, the lid is rotated relative to the tank such that the threads move in rotational disengagement. As the lid is removed, the neck 38 of the tank is moved out of the annular channel 144. After the neck passes out of the annular channel 144, and the seal 120 is completely disengaged from the interior surface of the neck 38, the resilient exterior lip 128 of the seal shifts away from the annular trench 138 and returns to its equilibrium position.

Figure 11A:
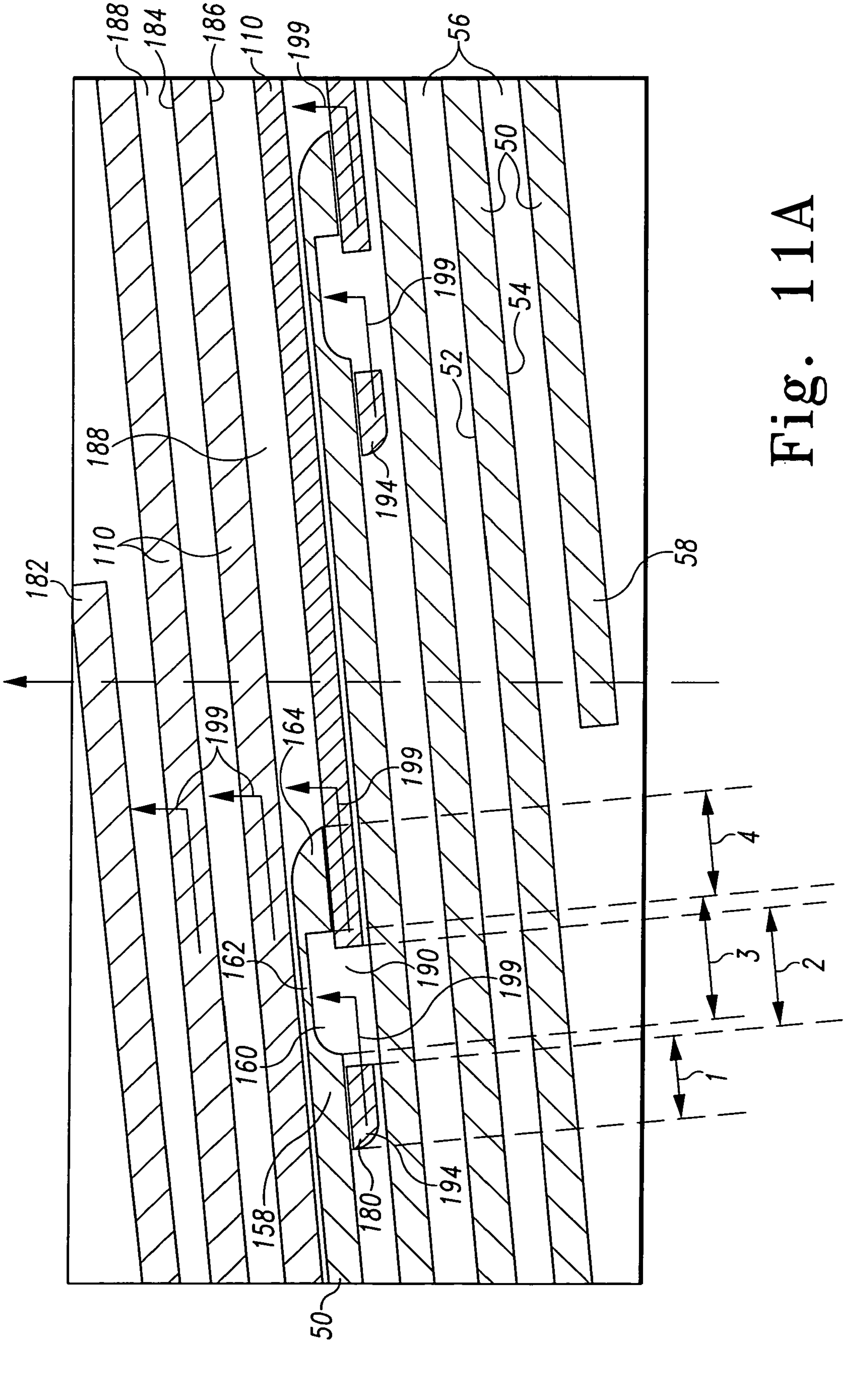
FIG. 11A shows a linear projection of threads on the lid and tank of the pressurized tank sprayer of FIG. 1 just before the lid is released from the tank.
Figure 11B:
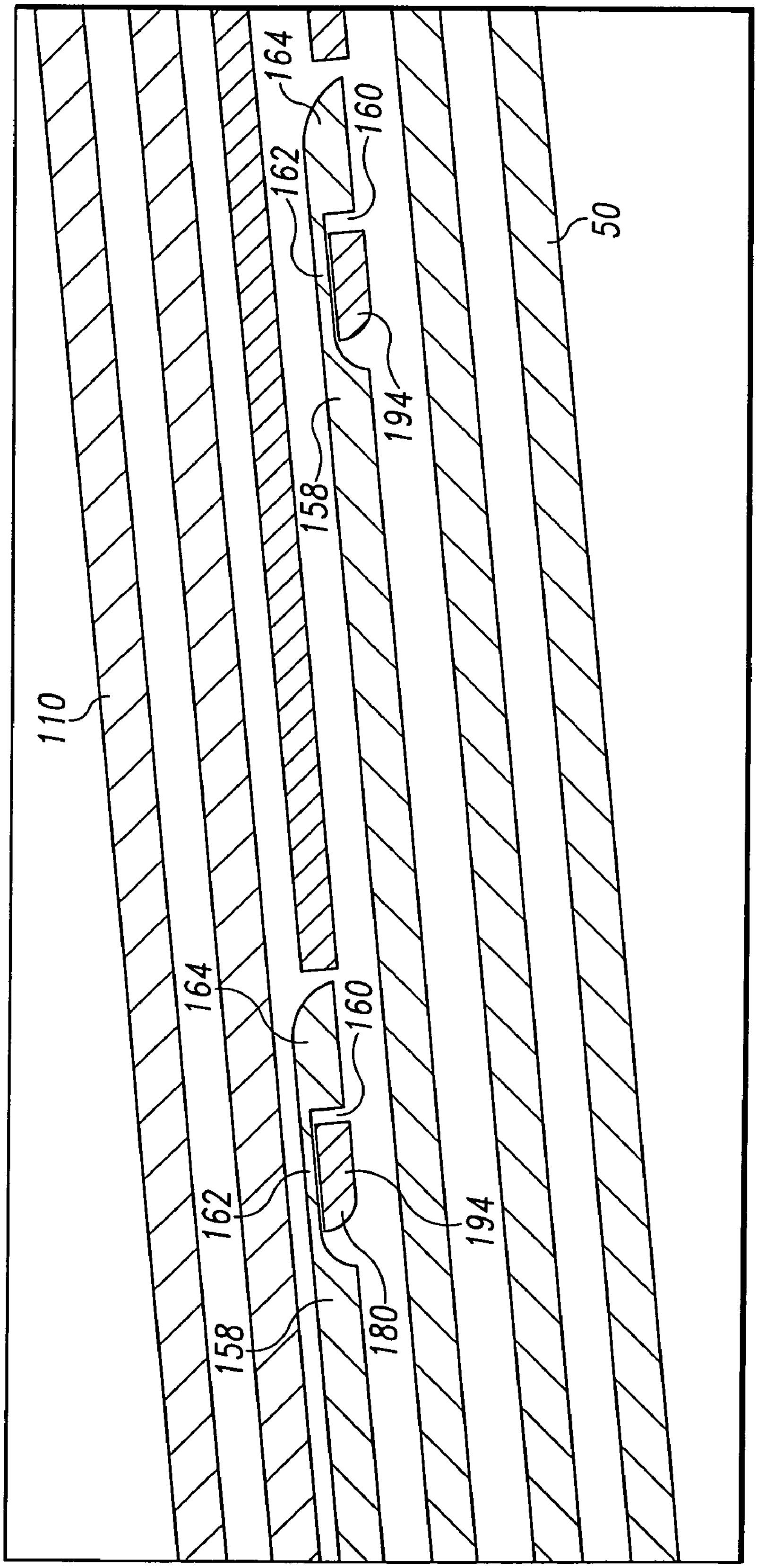
FIG. 11B shows a linear projection of the threads of FIG. 11A with the threads of the lid axially displaced from the threads of the tank.

In one alternative embodiment, the pressurized tank sprayer includes a locking thread feature that allows excess pressure inside the tank that is greater than atmospheric pressure to escape the tank before the threads on the tank and the threads on the lid are completely disengaged. With reference to FIGS. 11A and 11B, a linear projection is shown of the neck threads 50 of the tank 14 partially engaged with the skirt threads 110 of the lid over approximately 180° of the annular surface of the neck and skirt. The neck threads 50 of the tank 14 are shown with cross-hatching from right to left. The skirt threads 110 are shown with cross-hatching from left to right.

The neck threads 50 are formed on the exterior surface of the neck of the tank, are helical in shape, and spiral downward around the neck. Each neck thread includes a starting portion 158 at one end of the thread nearest the mouth, and an ending portion 58 at the opposite end of the thread. Also, each neck thread includes a mouth side 52 and a bottom side 54. A plurality of grooves 56 are formed between the neck threads such that a groove is formed between the bottom side of a thread and the mouth side of an adjacent thread. The grooves 56 expose the surface of the tank between the neck threads and provide tracks for receiving the skirt threads on the lid. The neck threads typically have a V-shaped cross-section, with the tip of the V pointing away from the tank. However, the threads may have other cross-sectional shapes, as will be readily recognized by those of skill in the art.

A recess 160 is formed in the starting portion 158 of each neck thread 50. Each recess 160 has a depth that extends from the bottom side 54 of the thread toward the mouth side 52, and exposes additional exterior surface of the neck where the thread would otherwise be. Each recess 160 separates a starting tip 164 of each neck thread from the remainder of the thread. A bridge portion 162 is positioned above each recess 160 to connect the starting tip 164 to the remainder of the thread. Thus, each neck thread 50 remains continuous from start to finish, as the bridge portion 162 spans across the recess in each thread. With continued reference to FIG. 11A, the length of each recess 160 is shown as $l_3$ and the length of the starting tip 164 of each neck thread 50 is shown as $l_4$.

The skirt threads 110 are formed on the interior surface of the skirt 62. The skirt threads 110 are helical in shape and spiral upward around the skirt interior. Each skirt thread 110 includes a starting portion 180 at one end of the thread nearest the bottom of the skirt, and an ending portion 182 at the opposite end of the thread nearer the top of the skirt. Also, each skirt thread 110 includes a top side 184 and a bottom side 186. A plurality of grooves 188 are formed between the neck threads 110 such that a groove is formed between the bottom side 186 of one thread and the top side 184 of an adjacent thread. The grooves 188 expose the interior surface of the lid between the skirt threads and provide tracks for receiving the neck threads 50 on the tank. Like the neck threads, the skirt threads 110 typically have a V-shaped cross-section, with the tip of the V pointing inward from the annular skirt. However, the threads may have other cross-sectional shapes, as will be readily recognized by those of skill in the art.

A cut-out portion 190 is formed in each skirt thread 110 near the starting portion 180 of the thread. The cut out portion 190 forms a void in the path of the thread 110 and exposes the interior surface 101 of the skirt where the thread would otherwise be. The cut out portion 190 extends from the bottom side 186 of the thread 110 to the top side 184 of the thread. Each thread separates a starting tip 194 of the thread from the remainder of the thread. Because of the cut out portions 190 in the skirt threads 110, and because no bridges span across the cut out portions 190, the skirt threads are not continuous from start to finish. FIG. 11A shows that the length of each cut-out portion 190 is defined as $l_2$ and the length of each starting tip 194 of the skirt thread 110 is defined as $l_1$.

The arrangement of the recesses 160 in the neck threads 50 and cut-out portions 190 in the skirt threads 110 provide the pressurized tank sprayer with a locking thread feature that permits and axial shift between the neck threads and the skirt threads. This axial shift allows excess pressure inside the tank that is greater than atmospheric pressure to escape the tank before the threads on the tank and the threads on the lid completely disengage. In particular, when the lid 16 is rotated in a counter-clockwise direction relative to the tank 14, the skirt threads 110 will begin rotational disengagement from the neck threads 50 as the lid begins to remove from the tank. If pressure remains in the tank when the lid 16 is being removed from the tank 14, the pressure in the tank will tend to force the lid away from the mouth of the tank. Accordingly, the top side 184 of the skirt threads 110 will be forced upward against the bottom sides 54 of the neck threads 50. However, just before the skirt threads 110 disengage from the neck threads 50, the starting portions 158 of the neck threads 50 will encounter the starting portions 180 of the skirt threads 110. As the starting tips 194 on the starting portions 180 of the skirt threads 110 encounter the recesses 160 on the neck threads 50, the pressure in the tank will force the starting tips 194 upward into the recesses 160. At the same time, the cut out portions 190 on the skirt threads 110 will receive the starting tips 164 of the neck threads 50. As the starting tips 194 on the lid engage the recesses 160 on the tank and the starting tips 164 on the tank engage the cut-out portions on the lid, the pressure in the tank causes the lid to shift axially upward and away from the tank without complete disengagement of the threads. This axial shift is represented in FIG. 11A by arrows 199. The shifted position of the threads is shown in FIG. 11B. Although the distance of the axial shift is only as deep as the depth of the recess 160 in the neck thread 50, this distance is sufficient to allow the pressurized air within the tank to escape from the tank. At the same time, the features on the starting portions of threads prevent the lid from being completely removed from the tank. Once the pressurized air has escaped, and the pressure within the tank returns to atmospheric pressure, the skirt threads 110 drop down from the position in FIG. 11B and rest in the grooves 56 of the neck. Additional counter-clockwise rotation of the lid relative to the tank causes the starting tips 194 of the skirt threads to pass by the starting tips 164 of the neck threads, and the lid is released from the tank. Accordingly, even if the user of the pressurized tank sprayer 12 fails to engage the pressure release valve 20 and release excess pressure within the tank prior to removal of the lid from the tank, any excess pressure will not cause the lid to become forcibly detached from the tank.

In general operation of the pressurized tank sprayer 12, the tank is first filled with a liquid to be dispensed from the nozzle 28. When the lid 16 is to be secured on the tank 14, the lid is placed over the mouth of the tank and the lid is rotated in the clockwise direction. Clockwise rotation of the lid causes the starting tips 194 of the skirt threads 110 to enter the grooves 56 on the neck. As the lid is rotated, the bottom side 186 of the skirt threads typically rest on the top or mouth side 52 of the neck threads because of the downward pull of gravity. Continued clockwise rotation causes the neck threads and skirt threads to fully engage as the top rim 40 of the tank becomes seated in the annular channel 144 formed in the lid, as shown in FIG. 10.

Once the lid is secured to the tank, the annular seal 120 provides a seal between the lid and the tank. Because the tank is sealed, air is prevented from escaping from the tank. The user then operates the pump 18 to introduce additional air into the tank. The additional air introduced into the tank increases the pressure within the tank. As explained previously, as pressure increases within the tank the pressure provides a force against the concave interior surface 132 of the annular seal 120, thereby maintaining secure contact between the annular sealing surface 136 and the skirt interior surface 103. The increased pressure within the tank forces liquid through the tube 24 and out of the nozzle 28 when the user operates the nozzle.

Following use of the pressurized tank sprayer 12, the user opens the pressure relief valve 20 to remove excess pressure from the tank. The user then rotates the lid in a counterclockwise direction to remove the lid from the tank. However, as discussed previously, if the user fails to open the pressure relief valve before removing the lid, the locking features of the threads, including the recesses and cut-outs on the starting portions prevent the lid from becoming forcibly detached from the tank.

Although the present invention has been described with respect to certain preferred embodiments, it will be appreciated by those of skill in the art that other implementations and adaptations are possible. Moreover, there are advantages to individual advancements described herein that may be obtained without incorporating other aspects described above. Therefore, the spirit and scope of the appended claims should not be limited to the description of the preferred embodiments contained herein.

What is claimed is:

1. A tank sprayer comprising:

a. a tank defining an interior chamber and having a mouth configured to provide access to the interior chamber, the tank further including a neck portion defining the mouth, and the neck portion having an interior neck surface and an exterior neck surface;

b. a lid configured to cover the mouth of the tank when the lid is secured to the tank, the lid including (i) a top portion, (ii) an annular wall depending from the top portion, the annular wall having an outer annular wall surface and (iii) a skirt depending from the top portion and having an interior skirt surface, the skirt being spaced apart from the annular wall to define an interior space therebetween, c. a seal positioned within the space and having a first lip, a second lip that is spaced apart from said first lip, and a transverse body portion connected between said first lip and said second lip; and d. a pump configured to advance air into the interior chamber of the tank, wherein said top portion of said lid includes a ramp structure that projects into said interior space with a curved profile to define a ramped seal seat surface, wherein, when (i) said transverse body portion is positioned in contact with said ramped seal seat surface, and (ii) said first lip is positioned in contact with said outer annular wall surface, said seal extends beyond said ramped seal seat surface so as to position said second lip in contact with said interior neck surface at a seal location, and wherein (i) a first gap is defined between said second lip and said interior neck surface on a first side of said seal location, and (ii) a second gap is defined between said second lip and said interior neck surface on a second opposite side of said seal location.

2. The tank sprayer of claim 1, wherein:

the skirt has a first plurality of threads formed on the interior skirt surface, the neck portion has a second plurality of threads formed on the exterior neck surface, and the first plurality of threads is configured to meshingly engage with the second plurality of threads.

3. The tank sprayer of claim 2 wherein the first plurality of threads and the second plurality of threads include means for permitting an axial shift of the first plurality of threads relative to the second plurality of threads in response to an increased pressure within the tank during rotatable disengagement of the first plurality of threads relative to the second plurality of threads, said axial shift permitting said increased pressure to be released from the tank without disengagement of the first plurality of threads from the second plurality of threads.

4. The tank sprayer of claim 1, wherein:

the first lip of the seal is spaced apart from the second lip of the seal so as to define a void therebetween, and the void is in fluid communication with the interior chamber of the tank, whereby an increase in pressure in the interior chamber causes an increase in pressure in the void.

5. The tank sprayer of claim 1, wherein the pump is attached to the lid.

6. A tank sprayer comprising:

a tank having (i) an interior chamber, (ii) a first opening configured to provide access to said interior chamber, and (iii) a neck portion defining said first opening and having an interior neck surface and an exterior neck surface;

a lid configured to cover said first opening when said lid is secured to said tank, said lid having a fluid port and including (i) a top portion, (ii) an annular wall depending from said top portion, said annular wall having an outer annular wall surface, and (iii) a skirt depending from said top portion and having an interior skirt surface, said skirt being spaced apart from said annular wall to define an interior space therebetween;

a seal positioned within said space and having a first lip, a second lip that is spaced apart from said first lip, and a transverse body portion connected between said first lip and said second lip;

a pump attached to said lid and configured to advance air into said interior chamber of said tank; and a hose assembly including (i) a hose positioned in fluid communication with said fluid port of said lid, and (ii) a nozzle in fluid communication with said hose, wherein said top portion of said lid includes a ramp structure that projects into said interior space with a curved profile to define a ramped seal seat surface, wherein, when (i) said transverse body portion is positioned in contact with said ramped seal seat surface, and (ii) said first lip is positioned in contact with said outer annular wall surface, said seal extends beyond said ramped seal seat surface so as to position said second lip in contact with said interior neck surface at a seal location, and wherein (i) a first gap is defined between said second lip and said interior neck surface on a first side of said seal location, and (ii) a second gap is defined between said second lip and said interior neck surface on a second opposite side of said seal location.

7. The tank sprayer of claim 6, wherein:

said skirt has a first plurality of threads formed on said interior skirt surface, said neck portion has a second plurality of threads formed on said exterior neck surface, and said first plurality of threads is configured to meshingly engage with said second plurality of threads.

8. The tank sprayer of claim 6, wherein:

the first lip of the seal is spaced apart from the second lip of the seal so as to define a void therebetween, and said gap is in fluid communication with said interior chamber of said tank, whereby an increase in pressure in said interior chamber causes an increase in pressure in said void.

9. The tank sprayer of claim 6, wherein said lid includes at least one handle configured to be grasped by a user.

10. The tank sprayer of claim 7 wherein said first plurality of threads and said second plurality of threads include means for permitting an axial shift of said first plurality of threads relative to said second plurality of threads in response to an increased pressure within said tank during rotatable disengagement of said first plurality of threads relative to said second plurality of threads, said axial shift permitting said increased pressure to be released from said tank without disengagement of said first plurality of threads from said second plurality of threads.

11. The tank sprayer of claim 1, wherein;

said ramped seal seat surface includes a concave ramped seal seat surface, and said transverse body portion of said seal includes a convex exterior body surface configured to mate with said concave ramped seal seat surface.

12. The tank sprayer of claim 1, wherein the interior skirt surface is positioned in contact with the exterior neck surface when the neck portion is positioned within the space.

13. The tank sprayer of claim 1, wherein:

said lid defines an annular recess formed around said annular wall, said annular recess is juxtaposed to said space, said seal further has a projection connected to said first lip, said projection being positioned in said annular recess, and said seal is generally h-shaped when said seal is viewed in a cross-sectional view.

14. The tank sprayer of claim 7, wherein;

said ramped seal seat surface includes a concave ramped seal seat surface, and said transverse body portion of said seal includes a convex exterior body surface configured to mate with said concave ramped seal seat surface.

15. The tank sprayer of claim 7, wherein the interior skirt surface is positioned in contact with the exterior neck surface when the neck portion is positioned within the space.

16. The tank sprayer of claim 7, wherein:

said lid defines an annular recess formed around said annular wall, said annular recess is juxtaposed to said space, said seal further has a projection connected to said first lip, said projection being positioned in said annular recess, and said seal is generally h-shaped when said seal is viewed in a cross-sectional view.

* * * * *